United States Patent [19]

Bird

[11] Patent Number: 5,165,398

[45] Date of Patent: Nov. 24, 1992

[54] VENTILATOR AND OSCILLATOR FOR USE THEREWITH AND METHOD

[76] Inventor: Forrest M. Bird, P.O. Box 817, Sandpoint, Id. 83864

[21] Appl. No.: 764,998

[22] Filed: Sep. 24, 1991

Related U.S. Application Data

[63] Continuation of Ser. No. 447,892, Dec. 8, 1989, abandoned.

[51] Int. Cl.$^5$ .................. A61M 16/00; A62B 7/00; A62B 9/02
[52] U.S. Cl. .................. 128/204.25; 128/205.23; 128/205.24
[58] Field of Search .................. 128/204.25, 204.18, 128/204.24, 204.26, 205.23, 205.24

[56] References Cited

U.S. PATENT DOCUMENTS

| | | | |
|---|---|---|---|
| 2,918,917 | 12/1959 | Emerson | 128/205.23 |
| 4,592,349 | 6/1986 | Bird | 128/204.25 |
| 4,805,613 | 2/1989 | Bird | 128/205.24 |
| 4,838,260 | 6/1989 | Bird | 128/205.24 |
| 4,867,151 | 9/1989 | Bird | 128/205.24 |
| 4,930,501 | 6/1990 | Bird | 128/205.24 |

Primary Examiner—Edgar S. Burr
Assistant Examiner—Kimberly L. Asher
Attorney, Agent, or Firm—Flehr, Hohbach, Test, Albritton & Herbert

[57] ABSTRACT

A ventilator in combination with a pneumatic oscillator cartridge comprising a body with an inlet, an outlet, a diaphragm operated valve, and a servo port. An adjustable valve is provided for metering the flow of gas from the outlet to the servo port to provide cyclic operation of the oscillator cartridge. A pneumatic clutching assembly is provided which has an inlet and an outlet. The outlet of the oscillator cartridge is connected to the inlet of the pneumatic clutching assembly. An oscillator canister is provided which has an inlet and an outlet. The outlet of the pneumatic clutching means is coupled to the inlet of the oscillator canister. The oscillator canister has a shaft, a diaphragm mounted on the shaft and separating the canister into first and second chambers. Countersprings are mounted on the shaft. The oscillator canister serves to supply and withdraw small volumes of gas to and from the patient adaptor. The small volumes of gas are superimposed upon the continuous flow of gas to the patient adaptor whereby dynamic volumetric diffusive ventilation is supplied to the patient.

36 Claims, 7 Drawing Sheets 5,165,398

VENTILATOR AND OSCILLATOR FOR USE THEREWITH AND METHOD

This is a continuation of application Ser. No. 07/447,892 filed Dec. 8, 1989, now abandoned.

This invention relates to ventilators and more particularly to pneumatically controlled ventilators and a method for providing dynamic volumetric diffusive ventilation to the airway of a patient.

Ventilators of various types have heretofore been provided. However, it has been found that such ventilators have not been capable of providing pneumatically controlled frequency modulation or high frequency superimposing of small volumes of gas upon the continuous as well as phasically flowing inhalation gases being supplied to the airway of the patient. There is therefore a need for a new and improved pneumatic ventilator which will provide such dynamic volumetric diffusive ventilation to the airway of the patient.

In general, it is an object of the invention to provide a pneumatic ventilator and method which provides dynamic volumetric diffusive ventilation to the airway of the patient.

Another object of the invention is to provide a ventilator and method which will deliver and retrieve tidal volumes through an independently selected baseline.

Another object of the invention is to provide a ventilator and method of the above character in which a constant or demand flow of gas is provided to the airway of the patient.

Another object of the invention is to provide a ventilator and method of the above character which can be utilized with interchangable breathing circuits to permit use in neonatal, pediatric and adult applications.

Another object of the invention is to provide a ventilator and method of the above character in which heated humidified gases can be supplied to the patient airway.

Another object of the invention is to provide a ventilator and method of the above character in which a selected demand constant positive airway pressure can be provided.

Another object of the invention is to provide a ventilator and method of the above character which makes it possible to selectively decrease peak-to-peak pressure bandwidths for weaning purposes.

Another object of the invention is to provide a ventilator and method of the above character in which negative and positive i/e and I/E ratios can be utilized during high frequency and low frequency cycling.

Another object of the invention is to provide a ventilator and method of the above character which can be utilized for minimizing intracranial bleeding and barotraumatic injury to the lungs of the neonatal patient.

Another object of the invention is to provide a ventilator of the above character which can be utilized as a stand alone ventilator.

Another object of the invention is to provide a ventilator which can be used in slaving another ventilator.

Another object of the invention is to provide a ventilator of the above character in which manometric readings can be obtained from the airway of the patient and/or a pneumatic oscillator cartridge for reading peak-to-peak pressure differentials.

Another object of the invention is to provide a ventilator of the above character in which a pressurized governor limits the pressures created in the airway of the patient.

Additional objects and features of the invention will appear from the following description in which the preferred embodiments are set forth in detail in conjunction with the accompanying drawings.

Figure 1:
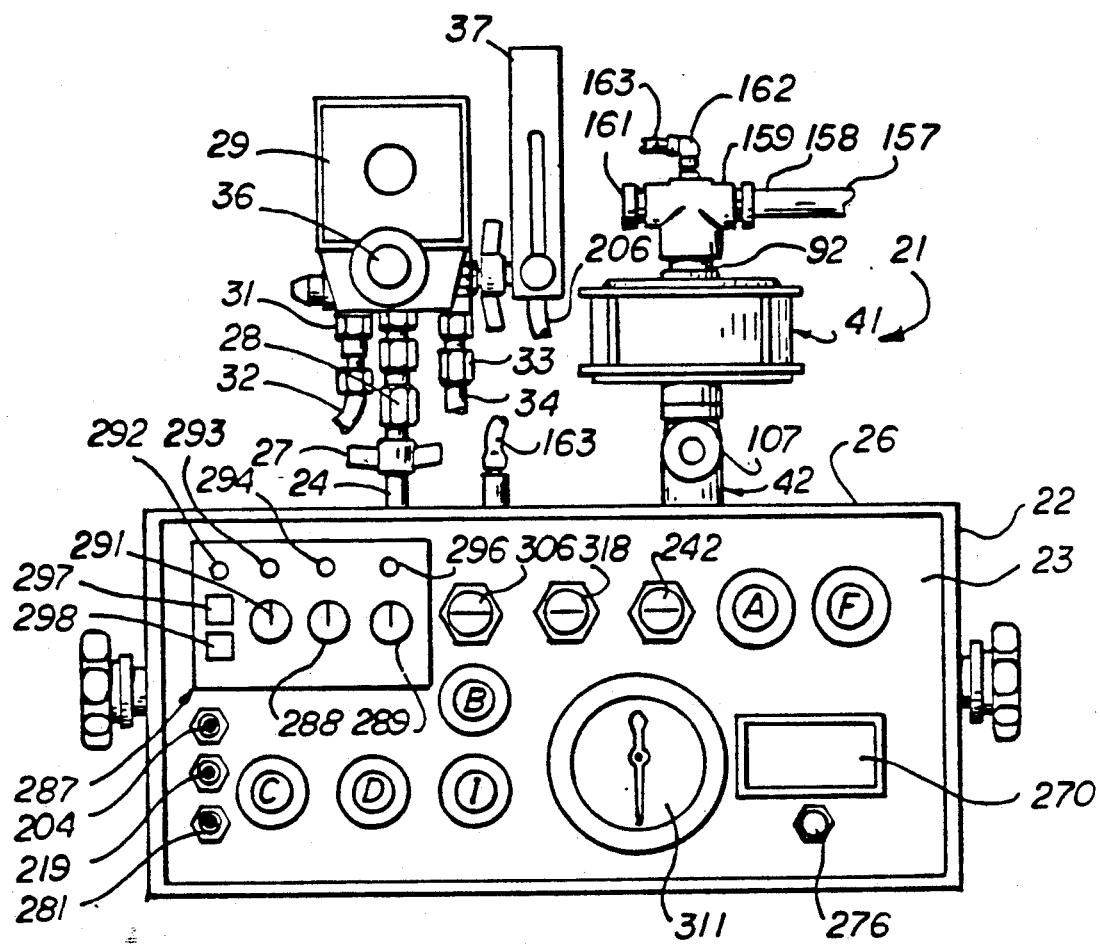
FIG. 1 is a front elevational view of a ventilator incorporating the present invention.

In general the ventilator of the present invention is adapted to be connected to a source of gas under pressure. A case is provided which has an inlet carried by the case and adapted to be connected to the source of gas. A pneumatic oscillator cartridge is mounted in the case and has a body with an inlet and an outlet and a flow passage interconnecting the inlet and the outlet. Diaphragm operated valve means is mounted within the body and is movable between open and closed positions for interrupting the flow of gas from the inlet to the outlet. A servo port is in communication with the diaphragm operated valve means and means is provided for supplying gas to the servo port. Adjustable valve means is provided for metering the flow of gas from the outlet to the servo port to provide cyclic operation of the oscillator cartridge. A patient adapter is provided which has an inlet. Means is provided for supplying a continuous flow of gas to the inlet of the patient adapter. Exhalation means is connected to the inlet of the patient adapter and permits gas to escape to ambient. Pneumatic clutching means is provided which has an inlet and an outlet. Means connects the outlet of the oscillator cartridge to the inlet of the pneumatic clutching means. An oscillator canister is provided which has an inlet and an outlet. Means couples the outlet of the pneumatic clutching means to the inlet of the oscillator canister. Means couples the outlet of the oscillator canister to the inlet of the patient adapter. The oscillator canister has a shaft. A diaphragm is mounted on the shaft and separates the oscillator canister into first and second chambers on opposite sides of the diaphragm with the first chamber being in communication with the inlet of the oscillator canister and the second chamber being in communication with the outlet of the oscillator canister. Counterspring means is mounted on said shaft. The oscillator canister serves to supply and withdraw small volumes of gas to and from the patient adapter. The small volumes of gas are superimposed upon the continuous flow of gas to the patient adapter so that dynamic volumetric diffusive ventilation is supplied to the patient.

In general, in the method for ventilating the airway of a patient from a source of gas under pressure, a continuous flow of source gas is supplied to the airway of the patient during the inspiratory phase of the patient. Gases from the airway of the patient are permitted to be discharged to ambient during the expiratory phase. Small volumes of gas are supplied to and withdrawn from the airway of the patient and are superimposed upon the continuous flow of source gas at a frequency which is substantially above the inspiratory and expiratory phases of the patient whereby dynamic diffusive ventilation is supplied to the airway of the patient.

The ventilator 21 of the present invention shown in FIGS. 1-4 consists of a case or housing 22 which is rectangular in form and which is provided with a front panel 23 removably mounted in the case 22. The case 22 is the same general type as described in U.S. Pat. No. 4,592,349. A rigid inlet tube 24 is mounted in the case 22 and extends upwardly through the top wall 26 of the case. A wing nut 27 is provided on the inlet tube 24 and is adapted to be connected to an outlet fitting 28 which is connected to and carries an oxygen blender 29. The oxygen blender 29 is of a conventional type such as described in U.S. Pat. No. 3,895,642. The oxygen blender 29 is supplied with oxygen and air in a conventional manner. Thus as shown, the blender is provided with an oxygen inlet fitting 31 which is connected to a tube 32 that is connected to a source of oxygen. Similarly, the blender 29 is provided with an air inlet fitting 33 that is connected by a tube 34 to a suitable source of air. The oxygen blender is provided with a control knob 36 by which the ratio of oxygen to air can be varied from 21% to 100%. A flow meter 37 of a conventional type is mounted on the oxygen blender 29 and measures the flow of the mixture of oxygen air passing through the outlet 28.

An oscillator canister 41 is provided that is mounted on the outlet of pneumatic clutching means 42 (PHASITRON) which is mounted within the case 22 and has its outlet 47 extending through the top wall 26 of the case 22. The PHASITRON pneumatic clutching means is described in detail in U.S. Pat. No. 4,592,349 beginning with line 36 of col. 46. As is described therein, it consists of a cylindrical hollow body 43 which has a cylindrical passage 44 extending therethrough. The passage 44 is in communication with an expiratory outlet 46. An additional outlet 47 in communication with the passage 44. The outlet 47 is plugged with a plug 48 and can be used for monitoring or other purposes. An outlet port 51 also is provided which is in communication with the passage 44. A venturi body 52 is provided which is slidably mounted within the body 43 and is yieldably urged upwardly as viewed in FIG. 4 by a spring 53. The venturi body 52 is provided with a venturi-like passageway 54 extending therethrough. The distal extremity of the venturi body 52 has an O-ring 56 mounted thereon which is adapted to engage an annular valve seat 57 provided in the body 43 which circumscribes the outlet port 51. A cap 58 is threaded onto the venturi body 52.

The cap 58 is provided with an orifice 59 which is in communication with a flow passage 61 provided in a diaphragm stem 62. The diaphragm stem 62 is carried by a diaphragm 63, the outer margin of which is clamped between the body 43 and an end cap 64. The end cap 64 is provided with an inlet flow passage 66 which is in communication with the flow passage 61. An O-ring 67 is provided which surrounds the stem 62 and permits slidable movement of the stem under the action of the diaphragm 63 while maintaining an airtight seal between the cap 58 and the stem 62. An inlet 68 is provided in the body 43 which is in communication with the passage 44 through the cap 58.

One leg of the tee 71 is mounted on the portion of the body 43 providing the outlet port 51 of the Phasitron 42. The oscillator canister 41 is mounted on the other leg of the tee 71 as shown in FIGS. 1-4 in such a manner so that the oscillator canister is in co-axial alignment with the Phasitron 42.

Figure 4:
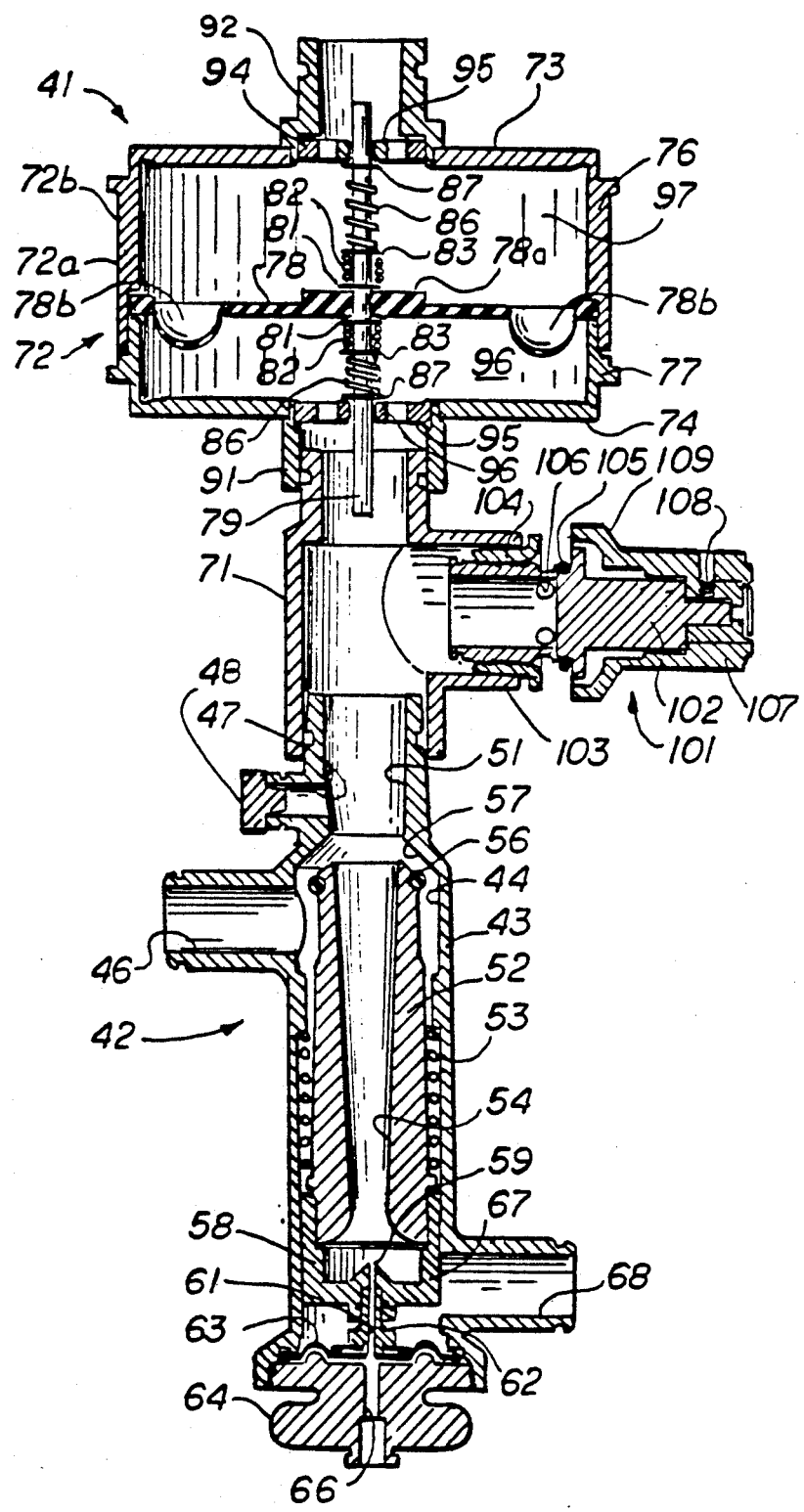
FIG. 4 is a cross sectional view of a pneumatic clutching means having an oscillator canister and spoiler which can be mounted thereon for use in the ventilator shown in FIG. 1.

The oscillator canister 41 consists of a housing 72 of two parts 72a and 72b formed of a suitable material such as a transparent plastic. The housing is provided with circular end pieces 73 and 74 with the end piece 73 being formed integral with a circular side wall 76 and end piece 74 being formed integral with a circular side wall 77. As shown in FIG. 4, the side walls 76 and 77 are adapted to be fitted together and sealed to each other by suitable means such as an adhesive to clamp therebetween the outer margin of a flexible diaphragm 78 formed of a suitable material such as NEOPRENE. This circular diaphragm 78 is provided with a central hub portion 78a through which shaft 79 extends and is retained thereon by C-rings 81 provided on opposite sides of the hub portion 78a and engaging the shaft 79. Damping means is provided on each side of the hub portion 78a of the diaphragm 78 and takes the form of a plurality of O-rings 82 provided on the shaft 79 on opposite sides of the hub portion 78a. The O-rings 82 are maintained in engagement with the C-rings 81 by additional C-rings 83 provided on the other side of the C-rings 81 and engaging the O-rings 82. Helical countersprings 86 are provided on the shaft 79 and are retained in engagement with the C-rings 83 by additional C-rings 87 mounted on the shaft 79.

The oscillator canister 41 is provided with an inlet fitting 91 that is mounted in the end wall 74 and outlet fitting 92 that is mounted in the end wall 73. Circular hubs 93 and 94 are mounted in the fittings 91 and 92 and have the through shaft 71 slidably mounted therein. Orifices 95 are provided in the hubs 93 and 94 which are in communication with a servoing chamber 96 on one side of the diaphragm 78 and a percussion chamber 97 provided on the other side of the diaphragm.

A spoiler 101 is mounted in the other leg or side port of the tee 71. The spoiler consists of a body 102 which is provided with a cylindrical extension 103 that is threaded into a hub 104 mounted in the tee 71. The cylindrical extension 103 is provided with a plurality of circumferentially spaced holes 106 which serve as flow passages to permit the escape of air from within the tee 71 to the outside ambient atmosphere. The amount of air escaping is controlled by adjustment of the body 102 by threading the body 102 into and out of the hub 104. An air-tight seal can be established by an O-ring 105 carried by the body 102 and adapted to establish a sealing engagement with the hub 104. A knob 107 is mounted on the body 102 and is retained thereon in a predetermined position by a set screw 108. The knob 108 is provided with calibrations on a rim 109 so that the position of the body 102 with respect to the openings 106 to permit the escape of air can be readily ascertained. By adjustment of the knob 108, it is possible to increase or decrease the amount of air escaping through the holes 106 and thereby decrease or increase peak-to-peak pressures while maintaining a constant oscillatory frequency at an associated inspiratory/expiratory (i/e) ratio.

Figures 5, 6:
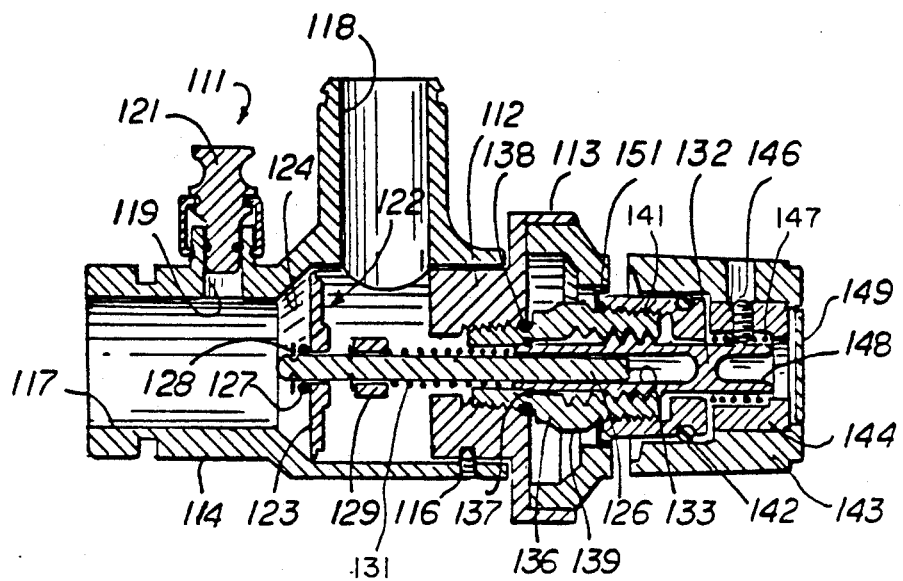
FIG. 5 is a cross sectional view of the pressure governor which can be utilized with the ventilator of FIG. 1.
FIG. 6 shows an oscilloscope trace from a waveform analyzer connected to the ventilator of FIG. 1 for supplying pneumatic volumetric diffusive ventilation to a patient.

A mean pressure rise governor 111 is provided to control maximum static breathing circuit pressures as hereinafter described. As shown in FIG. 5, it consists of a cylindrical body 112 which is provided with an upstanding flange 113. The body 112 and the flange 113 can be formed with suitable material such as brass. The body 112 is seated within a housing 114 and is retained therein by set screw 116. The housing 114 is provided with a regulation port 117 and an ambient outlet port 118. It is also provided with a service port 119 which is normally closed by a plug 121. A self centering gate 122 is provided within the housing 114 which consists of a circular plate 123 formed of suitable material such as plastic which is adapted to engage a seat 124 provided within the housing 114 to interrupt the flow between the regulation port 117 and the outlet port 118. The plate 123 is mounted on a valve stem 126 and is retained thereon by an O-ring 127 which is held in place by a C-ring 128 engaging the valve stem 126. A collar 129 formed of a suitable material such as plastic is mounted on the valve stem 126 and is engaged by a helical spring 131 mounted on the valve stem 126. The spring 131 is engaged by a valve stem follower 132 that is provided with a hole 133 into which the valve stem 126 extends. The valve stem follower 132 serves as a regulator shaft and is threadedly mounted in a valve stem hub 136 so that it can be adjusted longitudinally thereof. An O-ring 137 is provided at the lower extremity of the follower 132 to establish a sealing engagement between the hub 136 and the follower. The hub 136 is threaded into the body 112 and carries an O-ring 138 to establish a air-tight seal between the hub 136 and the body 112. The hub 136 is provided with a hex surface 139 to facilitate threading the hub 138 into the body 112. A cap 141 is threaded onto the hub 136 and has the valve stem follower 132 extending therethrough. An O-ring 142 is carried by the cap 141 and frictionally engages the control knob 143. The control knob 143 is provided with an insert 144 which is secured to the valve stem follower 132 by a set screw 146. A helical spring 147 is disposed on the valve stem follower 132 and extends between the insert 134 and the cap 141 and serves as an anti-backlash spring. An Allen head recess 148 for adjustable rotation of the valve stem follower 142 is provided in the outermost extremity of the valve stem follower 132. Access to the recess 142 is obtained through a removable end cap 149 provided on the control knob 143. A stop ring 151 is provided which is mounted on the hub 136 and serves to engage an abutment (not shown) and carried by the knob 143 to only permit rotation of the control knob 143 to 360° or one turn.

Figure 3:
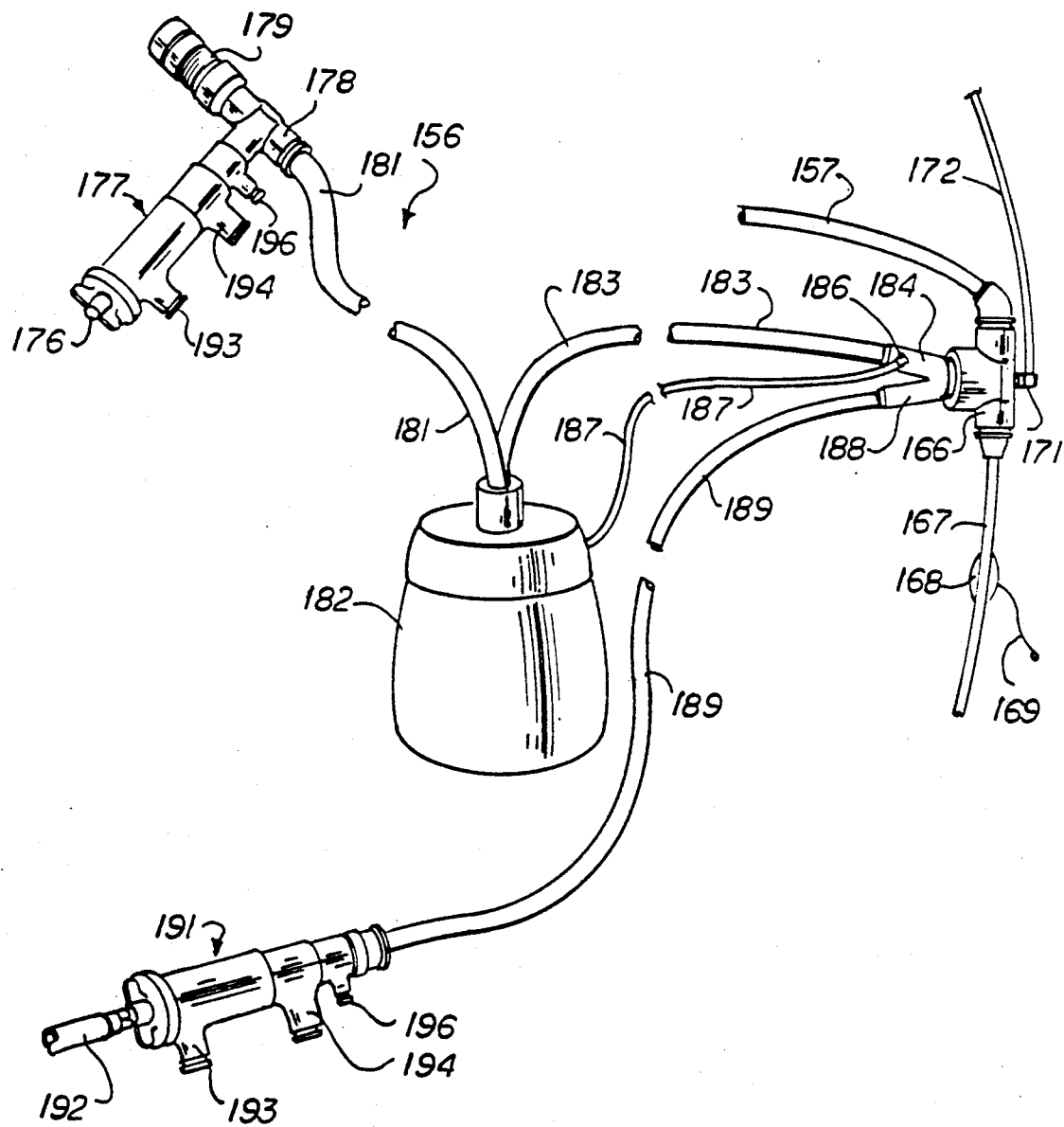
FIG. 3 is a perspective view of a pediatric/adult breathing circuit used with the ventilator shown in FIG. 1.

A pediatric/adult constant flow breathing circuit 156 for dynamic volumetric diffusive ventilation (DVDR) for use with the ventilator 21 is shown in FIG. 3. The breathing circuit 156 is provided with a main breathing tube which can be identified as percussion tubing 157 which is provided with a coupling 158 that is mounted in one leg of a tee 159 which has its side port mounted on the outlet fitting 92 of the oscillator canister 41. The other leg of the tee 159 is capped with a removable plug 161. A sampling port 162 is mounted in the tee 159 and is connected by tubing 163 to the interior of the case or housing 22. The tubing 157 is connected to a swivel tee 166 of the breathing circuit 156 and supplies pulsed gas as hereinafter described. The other leg of the swivel tee 166 is connected to a patient adapter 167 which takes the form of an endotracheal tube that is provided with a cuff 168 which is adapted to be inflated by a balloon inflation lumen 169. A sampling port 171 is provided on the swivel tee and is connected by tubing 172 to a port (not shown) provided on the rear side of the case 22 to make possible proximal airway pressure monitoring as hereinafter described.

A continuous flow of gas is provided to an orifice 176 of a PHASITRON pneumatic clutching means 177 of the type hereinbefore described. The outlet of the PHASITRON 177 is mounted in the side port of a tee 178. A pressure rise governor 179 of a conventional type is mounted in one leg of the tee 178 and tubing 181 which can be identified as the inspiratory circulation tubing is mounted in the other leg of the tee 178. The tubing 181 is connected to a heated humidifier 182 of a conventional type which supplies heated humidified gas through tubing 183 that is connected to one leg 184 of a swivel tee 166. A monitoring port 186 is mounted in the leg 184 and is connected by tubing 187 to the heated humidifier 182 to provide proximal airway heat sensing capabilities for the humidifier. The other leg 188 of the swivel tee 166 is connected by tubing 189 to a PHASITRON pneumatic clutching means 191 of a type hereinbefore described which is cycled through an inlet tube 192 in the manner hereinafter described. The PHASITRONS 177 and 191 are provided with inhalation and exhalation ports 193 and 194, respectably that are used for purposes hereinafter described. Each is also provided with a monitoring port 196 which is plugged when it is not used.

Figure 2:
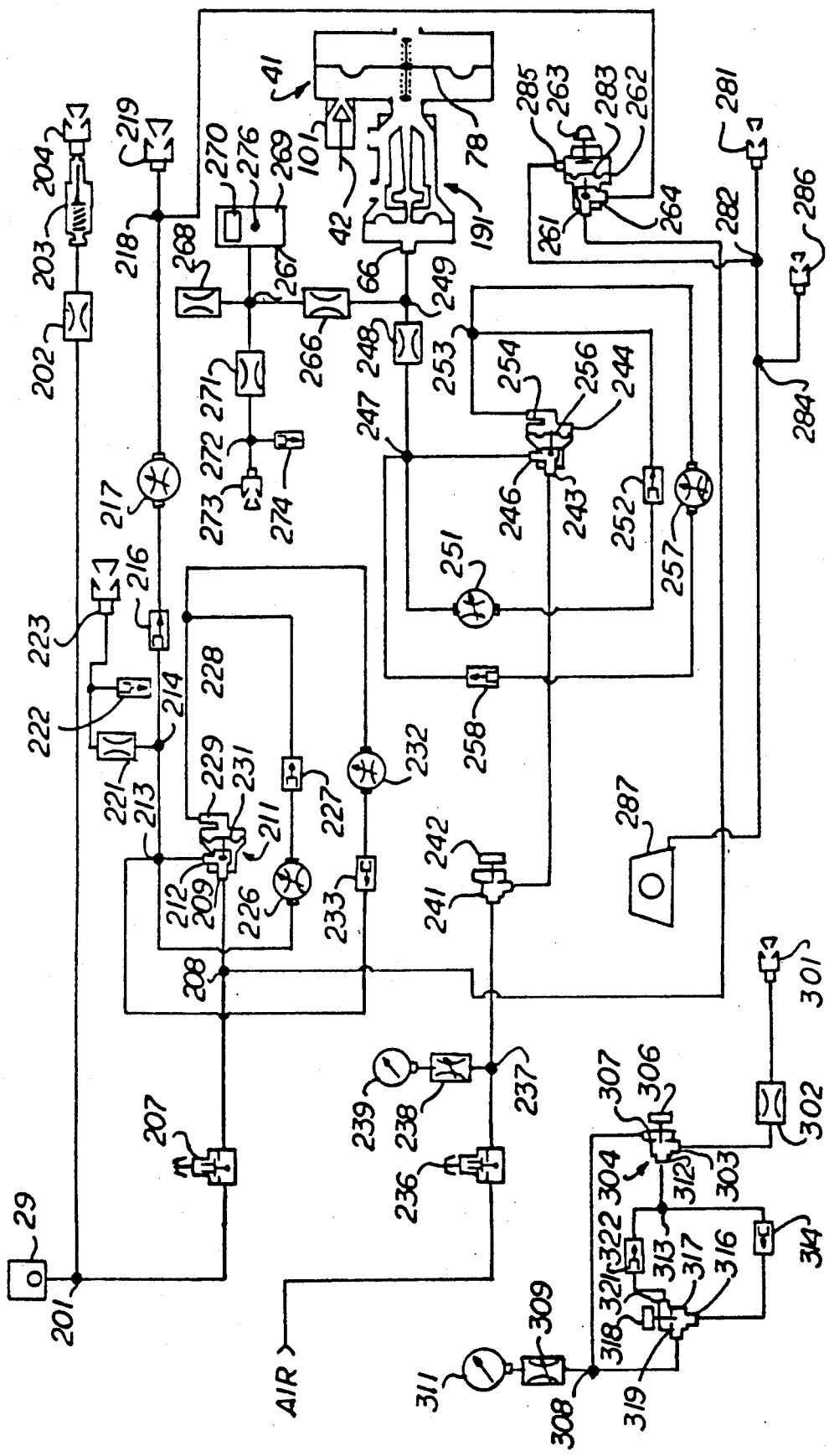
FIG. 2 is a schematic pneumatic diagram showing the major portion of the components of the ventilator in FIG. 1 and the interconnecting pneumatic circuitry utilized in the ventilator shown in FIG. 1.

Additional components which are a part of the ventilator 21 are provided within the case 22 and are shown schematically in the pneumatic circuit diagram shown in FIG. 2. These additional components are described in conjunction with the operation and use of the ventilator will be hereinafter described in conjunction with the pneumatic circuitry shown in FIG. 2. The ventilator 22 operates from two sources of respiratory gas, one oxygen, and the other air at a 50 pound operational source pressure with sufficient volume to cover up to 1.4 cubic feet of use per minute. As hereinafter explained, the ventilator 22 includes basically two separate respirators, one controls additional convective ventilation and the other controls dynamic oscillation of the respiratory gases supplied to the patient. Turning to the schematic shown in FIG. 2, the desired respirator gas is supplied from the oxygen blender 29 which permits selection of a ratio from 21 to 90% of oxygen supplied to a wye 201. One leg of the wye 201 is connected to a loading orifice 202 which is connected to a check valve 203. The check valve 203 is connected to a quick disconnect fitting 204 which is connected to tubing 206 (see FIG. 1) which is connected to the flow meter 37. The flow meter 37 can be selectively used and can be placed into service by utilizing the quick disconnect fitting 204 to open the check valve 203.

A continuous inflow of the source breathing gas is supplied through an 0.033 orifice (not shown) and is supplied to the orifice 176 of the PHASITRON 177 (see FIG. 3). Gas introduced into the PHASITRON 177 exits through the orifice 59 (see FIG. 4 and supplies pressure to the diaphragm 63 to move the diaphragm 63 and the venturi body 52 against the force of the spring 53 to close the exhaust port 46 to introduce a continuous flow of gas through the inspiratory tubing 181 to the heated humidifier 182. In the event of a pressure drop in the gas supplied through the inlet 176, the venturi body will be moved to open the gas exhaust port 46 under the force of the spring 53 to vent the tubing 181 to ambient and thereby provide a failsafe feature.

The other leg of the wye 202 is connected to a phasing pressure regulator 207 which is utilized to provide a regulated pressure of approximately 42 psi which is a conventional operational pressure for a ventilator. The outlet gas from the ventilator is connected to one leg of a tee 208. The other leg of the tee 208 is supplied to an inlet port 209 of a normally open pneumatic cartridge 211 which serves as a flow timing cartridge. With the cartridge 211 in open position, gas flows from the inlet 209 to the outlet 212 to one of four legs of a cross 213. Another leg of the cross 213 is connected to one leg of a tee 214. Another leg of the tee 214 is connected to an isolation check valve 216. The check valve 216 is connected to an inspiratory adjustable flow rate valve 217 which is provided with an adjustment knob identified as B in FIG. 1. The output from the flow rate valve 217 is supplied to one leg of a tee 218. Another leg of the tee 218 is connected to a quick disconnect fitting 219 of the type described in U.S. Pat. No. 4,592,349. The fitting 219 is connected to the tub 192 (see FIG. 3) which is connected to the PHASITRON 191. The flow rate valve 217 determines how fast gas flows into the lung of the patient during the inspiratory phase.

Gas is also supplied from the outlet 212 of the cartridge 211 through the tee 214 to a flow limiting orifice 221 of a suitable size such as 0.018 inches. The orifice 221 is connected to a balance check valve 222 and to a quick disconnect fitting 223. The fitting 223 is adapted to be connected via tubing (not shown) to an electronic waveform analyzer (not shown) of a conventional type sold by Percussionaire Corporation of Sandpoint, Id. The gas from the outlet 212 is also supplied from another leg of the cross 213 to an adjustable calibration valve 226 which can be identified as the I/E valve. The valve 226 is provided with a knob which is identified with the letter D as shown in FIG. 1 and is labeled "inspiratory phasing rate". The output from the calibration valve 226 is supplied through an uploading directional check valve 227 to the side port of a tee 228. One leg of the tee 228 is connected to the servo port 229 of the pneumatic cartridge 211 to supply gas to one side of the diaphragm 231 of the cartridge 211. After a period of time determined by the adjustment of the calibration valve 226, the diaphragm 231 will move the normally open pneumatic cartridge 211 from a normally open position to a closed position to interrupt the flow of gas from the inlet port 209 to the outlet port 212. This interrupts the flow of gas to the servo port 229 which is then bled down through the tee 228 through an adjustable phasing rate valve 232 that is adjusted by a knob identified with the letter C (see FIG. 1) and labeled the "expiratory phasing rate". The valve 232 downloads through a directional downloading check valve 233 through the cross 213 through the isolation check valve 216, the valve 217, the tee 218, the fitting 219 to the tubing 192 see FIG. 3) through the PHASITRON 191 to the atmosphere. Thus it can be seen that the adjustable valves 226 and 232 provide a timing circuit in which the valve 226 determines the length of the inspiratory phase and the valve 232 determines the length of the expiratory phase. The valves 226 and 232 provide a timed cycle respirator to provide convection type ventilation to the patient.

Another portion of the pneumatic circuitry shown in FIG. 2 controls the dynamic oscillation superimposed upon the normal convection pattern provided by the time-cycled ventilation portion of the pneumatic circuitry. Since oxygen is not needed for operating this portion of the pneumatic circuitry, source air is supplied to an operating pressure regulator 236 which is independent of the regulator 207 to supply air at an appropriate pressure as, for example, 42 psi to one leg of a tee 237. The side port of the tee 237 is connected to a dampening snubber orifice 238 of a suitable size as, for example, 0.013 inches to a meter 239 for measuring the percussive amplitude of the gas being supplied to the tee 237. The other leg of the tee 237 is connected to an on/off selector switch 241 which is provided with a knob 242 on the front panel for turning the oscillator component on and off. The switch is a conventional on/off rotary type. With the rotary switch 241 turned on, gas is supplied to the inlet port 243 of a normally open pneumatic cartridge 244. Gas is supplied to an outlet 246 to one leg of a cross 247. Gas is supplied from one leg of the cross 247 to a loading orifice 248 of a suitable size, such as 0.060 inches to one leg of a tee 249. Another leg of the tee 249 is connected to the inlet flow passage 66 of the PHASITRON 42 (see FIGS. 2 and 4). Another leg of the cross 247 is connected to an adjustable calibration valve 251. The calibration valve 251 can be identified as the percussion ratio i/e and is provided with a knob which is identified with the letter F on the front panel 23 (see FIG. 1). This knob F makes it possible to control the i component of the i/e ratio. Gas from the adjustable valve 251 is supplied to the uploading directional check valve 252 which is connected to the side port of a tee 253. One leg of the tee 253 is connected to the servo port 254 of the cartridge 244 and supplies gas to one side of the diaphragm 256 which after a predetermined period of time as determined by the adjustment of the valve 251 causes the diaphragm to move the cartridge 244 from a normally open position to a closed position to interrupt the flow of gas from the inlet 243 to the outlet 246. As soon as the flow of gas is interrupted, there is a bleed-down of the gas from the servo port 254 through the tee 253. The other leg of the tee 253 is connected through an oscillator frequency adjustable valve 257 that is provided with a control knob on the front panel 23 identified with the letter A for determining the oscillator frequency by determining the expiratory flow rate. Gas from the adjustable valve 257 is supplied through the directional downloading check valve 258 which is connected to one leg of the cross 247 and then through the loading orifice 248 to the inlet flow passage 66 of the PHASITRON 42 mounted on the case 22. Thus it can be seen that the convection timing circuit is bled down through one PHASITRON 42 whereas the diffusive oscillatory timing circuit is separately bled down through the PHASITRON 191.

Demand CPAP is provided in the ventilator 21 and utilizes the gas supplied from the side port of the tee 208 to the inlet port 261 of a demand CPAP regulator 262 of a conventional type. The regulator 262 is provided with a knob 263 which on the front panel 23 carries the letter I which can be moved from an "off" position to an "on" or increase position. Assuming that the CPAP regulator is on, gas is supplied from the inlet 261 through an outlet 264. This gas is delivered to the side port of the tee 218 to the phasing rate quick disconnect fitting 219 connected to the inlet tube 192 into the inlet passage of the PHASITRON 191 (see FIG. 3).

The oscillatory frequency of the diffusive oscillator timing circuit is measured by taking gas from the side port of the tee 249 as it is supplied through the loading orifice 248 through a flow limiting orifice 266 of suitable size such as 0.018 inches to one leg of a cross 267. Another leg of the cross 267 is connected through a balance orifice 268 of a suitable size such as 0.013 inches. Another leg of the cross 267 is connected to a battery operated frequency counter 269 of a conventional type which provides a digital readout 27° of the frequency in number of cycles per minute. Another leg of the cross 267 is connected through a flow limiting orifice 271 of a suitable size such as 0.021 inches that is connected to one leg of a tee 272. The other leg of the tee 272 is connected to a fitting 273. The fitting 273 is adapted to be connected to a wave form analyzer of the type hereinbefore described. The side port of the tee 272 is connected to a balance check valve 274. Thus frequency can be measured in the waveform analyzer and in addition, in the small battery operated frequency counter 269 which is mounted in the front panel 23. The frequency counter 269 is provided with a push switch 276 which can be depressed to cause the counter to register the frequency count. The counter 269 is provided with a readout 270.

In the ventilator of the present invention proximal airway pressure is measured. This is accomplished by taking the airway pressure in the swivel tee 166 at the port 171 supplied through the tube 172 (see FIG. 3) to a fitting 281 (see FIG. 2 . The fitting 281 is connected to one leg of a tee 282. The side port of the tee 282 is connected to a servo port 283 of the demand CPAP regulator 262 which causes servoing of a diaphragm 285 to maintain a constant positive airway pressure in the lungs of the patient. The other leg of the tee 282 is connected to one leg of a tee 284. The side port of the tee 284 is connected to a fitting 286 which is adapted to be connected to the wave format inlet of the wave form analyzer hereinbefore described. The other leg of the tee 284 is connected to a pressure drop/rise alarm 287. This pressure drop/rise alarm 287 is mounted in the upper left-hand corner of the panel 23 shown in FIG. 1. The alarm 287 sounds an audible alarm whenever the pressure drop or the pressure rise exceeds predetermined limits as determined by the settings on the pressure drop knob 288 and the pressure rise knob 289. The alarm 287 is also provided with time delay knob 291. The alarm 287 is also provided with four LED's 292, 293, 294 and 296 in which the LED 292 is an indication of breath, 293 an indication of low battery, 294 an indication of an unallowable pressure drop, and 296 an indication of an unallowable pressure rise. In addition, an on-off pushbutton 297 and a reset pushbutton 298 are provided.

The outlet from the oscillator canister 41 is monitored directly from the port 162 in the tee 159 provided in the oscillator canister 41 and is connected by the tube 163 (see FIG. 1) to a fitting 301. Gas supplied to the fitting 301 passes through a simulation orifice 302 of a suitable size such as 0.033 inches to an inlet 303 of a proximal pressure/peak-to-peak selector switch 304 that is provided with a knob 306 on the front panel 23 movable between "on" and "off" positions. Assuming that the switch 304 is in an "on" position, gas is supplied through an outlet port 307 to the side port of a tee 308. One leg of the tee 308 is connected through a dampening snubber orifice 309 of a suitable size such as 0.013 inches to a manometer 311 mounted in the front panel 23. The manometer 311 measures mean pressure, which pressure is controlled by the demand CPAP regulator 262. In addition, the manometer 311 gives the pressure rise and the pressure drop during convective ventilation. If the selector switch 304 operated through the knob 306 to measure peak-to-peak pressure rather than proximal airway pressure, gas is supplied from the inlet 303 through an outlet 312 through a side arm of a tee 313. One leg of the tee 313 is supplied to peak positive pressure isolation check valve 314 which is connected to the inlet 316 of a positive/negative selector switch 317 that has a knob 318 on the front panel 23. The knob 318 can select three positions of the three-way switch 317 and is labeled "proximal airway". The proximal airway is at the top and the peak-to-peak is at the right. Similarly, with respect to knob 306, the positive airway pressure is at the top and the positive-negative is to the right as viewed in FIG. 1. Thus, assuming that the knob 318 is moved to a position selecting peak-to-peak, gas under pressure is supplied through the check valve 314, through the inlet 316 to the outlet 319 to the other leg of the tee 308 through the snubber 309 and into the manometer and is 311. Gas is supplied to the manometer, trapped in the manometer but can bleed out very slowly. Thus the manometer 311 stays in the peak positive position. The positive-negative selector switch knob 306 is rotated to the negative position, the pneumatic circuit to the manometer is evacuated through gas being supplied from inlet 316 through an outlet 321 and through a peak sub-ambient isolation check valve 322 through one leg of the tee 313 and through the outlet 312 of the selector switch 304 through the outlet port 307 through the tee 308 to the dampening snubber 309. This provides a sub-ambient pressure reading on the manometer 311 which remains in position. Trapping both the peak positive and the peak negative sub-ambient pressures provides a mean reading on the manometer 311 which is the difference between the positive and negative pressures.

Referring to the breathing circuit shown in FIG. 3, percussion gas supplied from the oscillator canister 41 is delivered at a pulse rate which can vary from 0 to 1500 cycles per minute and typically approximately 900 cycles per minute to the swivel tee 166 and into the patient adapter 167 which takes the form of the endotracheal tube. These percussion gases are superimposed upon a continuous supply of gas which is delivered through a PHASITRON 177 that serves as a failsafe distribution manifold into the heated humidifier 182. The humidifier wets the gas supplied to the humidifier 182 and delivers the same to the inspiratory circulation tubing 183 where it is delivered to the swivel tee 166. The gases are also supplied to the expiratory circulation tubing 189 and to the PHASITRON 191. In this way, the entire breathing circuit is pressurized and causes gases to flow into the lungs of the patient through the endotracheal tube 167. Thus when the inlet tube 192 of the PHASITRON 191 is pressurized, gases will be supplied to the patient and when the inlet 192 is depressurized, the continuous flow of gas will flow out of the exhalation port 194. In this way, the PHASITRON 191 serves as a pneumatic clutch for controlling the flow of gas into the lungs of the patient. If the demand CPAP regulator 262 is in operation, this will supply gas under pressure to the tubing 192 which causes closure of the PHASITRON 191. Assuming a constant inflow of 20 liters per minute through the inspiratory circulation tubing 183 and by regulating the outflow from the PHASITRON 191, the patient must breath against a constant positive airway pressure as determined by the demand CPAP regulator.

In the event there is a failure of gases being supplied to the inspiratory circulation tubing 183 and in order to prevent the patient from rebreathing the same gases, fresh gas is supplied to the patient through the failsafe manifold provided by the PHASITRON 177. Exhalation gases are exhausted through the exhaust port 194 so that, fresh gas would be supplied to the patient from the port 194 although at a lower rate. This condition would be sensed and the alarm 287 would go off.

The pressure rise regulator 179 regulates the pressure in the inspiratory breathing circuit as hereinbefore described and also serves as a failsafe device which opens when an overpressure condition occurs.

Operation of the PHASITRON 42 in conjunction with the oscillator canister 41 to produce a typical waveform such as shown in FIG. 6 can now be briefly described as follows. In the pneumatic circuitry in FIG. 2 as hereinbefore described, the PHASITRON 42 under the control of the oscillator cartridge 244 can move backwards and forwards at frequencies up to 1500 times a minute. The frequency can be readily adjusted to a lower rate, as for example, down to 200 to 400 times a minute. Each time the diaphragm 63 (see FIG. 4) of the PHASITRON 42 is pressurized, the venturi body 53 slides forward to close off the exhalation port 46. Gas is then supplied to the servoing chamber 96 in the housing 72 of the oscillator canister 41. The diaphragm 78 is moved upwardly as viewed in FIG. 4 and relaxes the counterspring 86 on the servoing chamber 96 side and compresses the counterspring 86 in the percussion chamber 97 side. This causes a change or decrease in volume and increase in pressure in the percussion chamber 97 and the entire breathing circuit extending to the patient.

The PHASITRON 42 provides the pneumatic force to cause the forward stroke of the diaphragm 78. As soon as the PHASITRON 42 is depressurized, the venturi body 52 moves downwardly under the force of the spring 53 to open the exhalation port 96 and the gas within the servoing chamber 96 immediately rushes out and discharges through the exhalation port 96. The energy stored in the counterspring 86 above the diaphragm 78 as viewed in FIG. 4 forces the diaphragm 78 very rapidly downwardly to increase the volume and to create a vacuum or sub-ambient condition within the chamber 97 and in the breathing circuit. This sub-ambient condition is terminated as soon a gas under pressure is supplied to the inlet flow passage 66 of the PHASITRON 42 to again move the venturi body 52 upwardly as viewed in FIG. 4 to close the exhalation port 46 and again cause pressurization of the servoing chamber 96 of the diaphragm 78 upwardly. These constant stroke movements of the diaphragm 78 between the two positions occur very rapidly to cause the oscillator canister 41 to supply and withdraw small volumes of gas to and from the patient adapter. Very high frequency operation is possible because there is very little inertia in the diaphragm 78 and the shaft 79. The rapid changeover from one condition to the other is different from a piston-like movement in which the changeover is very slow when moving over the top of dead center.

In the operation of the oscillator canister 41 it should be appreciated that the annular convolution 78b provided in the diaphragm 78 serves a particular function. When pressure is applied to the servoing chamber 96 the convolution 78b rolls or is deformed into the chamber 97 because of its thinner cross section in advance of any substantial movement of the diaphragm 78 to provide a percussive change (decrease) in volume in the chamber 97. Translation of the central portion 78a of the diaphragm 78 follows. It is desirable that the portion 78b of the diaphragm 78 be relatively thin so it offers very little resistance to a change in pressure in either the chambers 96 or 97. In addition, the convolution 78b must be very elastic and be capable of long periods of use without failure. By way of example, 70 durometer rubber used for such a diaphragm with a relatively thin convolution 78b as for example, a thickness of 0.015 inches has been utilized with success.

If the ventilation of the patient is being undertaken with a substantially constant pressure from the breathing circuit, the hub 78a of the diaphragm 78 will tend to seek a center position. As the pressure rises in the chamber 96, the hub 78a is moved further to the right to further compress the counterspring 86 in the chamber 97. However, the pressure rise in the chamber 97 will tend to force the central portion 78a of the diaphragm 78 to the left to compress the counterspring 86 on the left hand side of the diaphragm 78 until the centered position is achieved. Depressurization of the chamber 96 will cause a similar movement of the diaphragm in the opposite direction. The motion of the convoluted portion 72b will always proceed that of the central portion 78a because of its greater flexibility and therefore greatly aids in creating the rapid pressure changes occurring in the chambers 96 and 97. This makes it possible to provide the same amplitude of stroke of the through shaft 79 independent of the pressure created in the breathing circuit. There is provided a constant adjustable percussive stroke which is caused by indexing and reindexing of the convolution 78b of the diaphragm 78 as the central portion 78a of the diaphragm 78 travels with the mean pressure created.

From the waveform 334 which is shown in FIG. 6 which is calibrated in the abscissa from 0 to 40 centimeters of water and in the ordinate in cycles per minutes with reference to a curve or trace 331 which shows pips 332 having a repetition rate with a paper or chart speed of 25 millimeters per second. When the PHASITRON 191 moves to an open position, the patient passively exhales through the exhalation port 194 to ambient or to an established baseline as indicated by the baseline portion 336 of the waveform 334 shown in FIG. 6. As soon as the PHASITRON 191 is time cycled to a closed position in the manner hereinbefore described, at a continuous adjustable cyclic rate inspiratory circulating gases in the tube 181, at flow rates varying from 10 to 60 and preferably 20 liters per minute are supplied to the heated humidifier 182. Nebulized gases are then supplied through the tubing 183 to build up a pressure in a gradual manner in the manner shown, by the portion 337 of the waveform 324. When the PHASITRON 191 opens, the patient exhales through the exhalation port 194 and the pressure drops relatively rapidly as shown by the portion 338 of the waveform 334 in FIG. 6. This pressure drop continues until a base line portion 336 which can be ambient as shown in FIG. 6 or at a predetermined pressure above ambient as provided by the CPAP regulator 262. The portions 337 and 338 of the waveform 334 shown in FIG. 6, are the time cycled convection type ventilation provided by the calibration cartridge 211 controlled by metering valves 226 and 232 and can vary from 1 to 55 breaths per minute. Superimposed upon this convection type waveform 334 shown in FIG. 6 are high frequency percussive pulses 341 at a frequency rate typically ranging from 300 to 1500 times a minute. These high frequency pulses or small volumes of gas or percussive pulse 341 are superimposed upon all portions of the waveform 334 shown in FIG. 6 and are effective throughout all portions of the waveform 334 as shown in FIG. 6. It is important to note that the oscillatory pulses which are applied to the waveform in FIG. 6 do not fade out near the top of the waveform but have a substantially constant amplitude throughout the curve as shown in FIG. 6. With the oscillator canister 41 of the present invention it has been found that the small volume of gas constitutes approximately five cubic centimeters of gas which are pulled into and out of the breathing circuit by oscillation of the diaphragm 78. The size of the small volumes of gas can be adjusted by increasing or decreasing the amount of gas supplied to the servoing chamber 96. The small volumes of gases moved back and forth in the breathing circuit can be varied from as little as 1 or 2 cubic centimeters to as many as 50 cubic centimeters.

The oscillator canister 41 in effect is substantially instantaneously first pressurizing the breathing circuit and then substantially instantaneously providing cavitation in the breathing circuit. The use of the countersprings 86 in conjunction with the diaphragm 78 makes it possible to obtain a substantially constant stroke volume. As pressure builds up within the oscillator canister 41, the hub portion 78a of the diaphragm is adjusted or reset just like in a regulator to provide a constant stroke volume. It is the positioning of the convolution 78b which provides the rapid changes in pressure that remain substantially constant regardless of the energy which is driving the PHASITRON 42.

The spoiler 101 which is connected to the PHASITRON 42 is in communication with the outlet of the PHASITRON and is provided to make it possible to leak air to ambient from between the venturi body 52 and the diaphragm 78 of the oscillator canister. For example, if it is desired to decrease the peak pressure from 60 centimeters of water down to 20 centimeters of water or any lower pressure, the knob 107 can be operated to permit a desired quantity of air to leak through the holes 106 to ambient as shown in FIG. 4 so that the desired peak pressure is reached. This makes it possible to obtain a desired mean pressure without changing the phasing rate or any of the programming which has previously been set up in the ventilator 21. For example, it is possible to have a 900 cycle per minute phasing rate for the oscillator canister 41 with a predetermined I/E ratio as, for example, 1:1.5 to provide a constant amplitude.

The spoiler 101 is particularly useful when weaning a patient from a ventilator. The spoiler 101 makes it possible to lower the amplitude of the percussive waves which are supplied to the breathing circuit since the amplitude of the time cycled dynamic convective or volumetric diffusive ventilation would be decreased after which the amplitude of the oscillatory pulses supplied would be decreased. Finally the patient would be weaned onto demand CPAP to reestablish the respiratory musculature of the patient.

Figure 7:
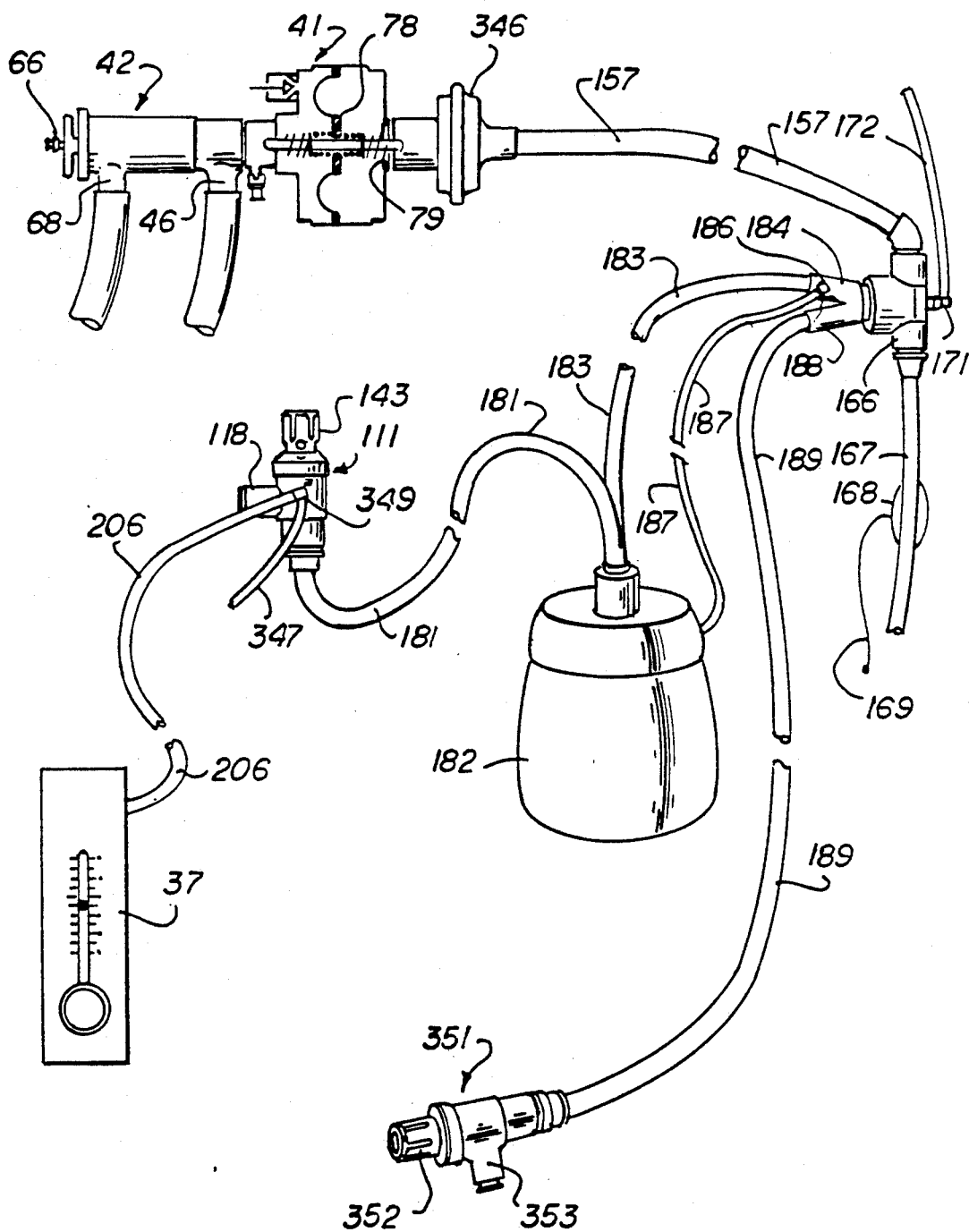
FIG. 7 is a perspective view of another breathing circuit for us in the ventilator shown in FIG. 2 particularly adapted for use in neonatal applications and utilizing the pressure govenor shown in FIG. 5.

The ventilator 21 of the present invention can also be utilized with a constant flow neonatal breathing circuit such as shown in FIG. 7. It is in many respects very similar to the pediatric/adult breathing circuit shown in FIG. 3. The principal difference is that a pressure rise governor 111 of the type shown in FIG. 5 has been utilized as an overpressure device in place of the failsafe PHASITRON distribution manifold 177. A bacteria filter 346 has been provided at the output of the oscillator canister 41 and is connected to the percussion tubing 157. In the neonatal breathing circuit, a metered inflow of gas, as for example, 5 to 9 liters per minute is applied through a tube 347 into a fitting 349 mounted in the service port 119 (see FIG. 5) through the pressure rise governor 111 which is set at a predetermined pressure as, for example, 42 cm $H_2O$ to deliver gas into the inspiratory circulation tubing 181 to the heated nebulizer/humidifier 182. The nebulizer/humidifier 182 wets and/or heats the gases and supplies the same to the tubing 183 which supplies the gases to the swivel tee 166 in the manner hereinbefore described. The gases are also supplied to the expiratory circulation tubing 189 through an adjustable outflow valve 351 which has been used in place of the PHASITRON 191 in FIG. 3. The adjustable outflow valve 351 is 351 of a conventional type and is a spring loaded directional valve which has a relatively stiff spring constant that can be adjusted by the knob 352 to provide an adjustable spring-loaded gate. Outflow will occur from a port 353 when a predetermined pressure as, for example, 10 to 25 centimeters of water is reached in the expiratory tubing 189. When a PHASITRON is in the exhalation circuit, there is a gradual pressure rise. When an adjustable outflow valve 351 is utilized there is a sharp percussive pressure rise because of the relatively stiff spring yield in the adjustable out flow valve which does not near instantaneously collapse because of high spring rate. This rapid pressure rise is shown by the waveform 361 in FIG. 8 in which it can be seen that the pressure rises to a maximum pressure, as for example, 40 centimeters of water. Similarly after an appropriate interval of time, after the outflow valve opens to permit gas to flow through the port 353 there is a rapid drop in pressure. The pressure drops to a mean pressure, as for example, 20 centimeters of water, as shown at 362 in FIG. 8. This mean pressure is determined by the spring adjustment on the outflow valve 351. Increasing the spring pressure on the outflow pressure valve increases the mean pressure that would be established against the neonatal breathing circuit shown in FIG. 7. In this way, constant pressure at all times can be provided in the breathing circuit in the same manner as established by the demand CPAP regulator 262. When a sudden pressure rise strikes the gate of the adjustable outflow valve, the spring yieldably retains a CPAP pressure rise on the breathing circuit, as shown in the waveform 361 in FIG. 8. Superimposed upon this continuous flow of gas in the inspiratory circuit 183 is the percussive flow from the tubing 157 supplied from the oscillator canister 41 at a rate of 300 to 1500 cycles per minute.

Figure 8:
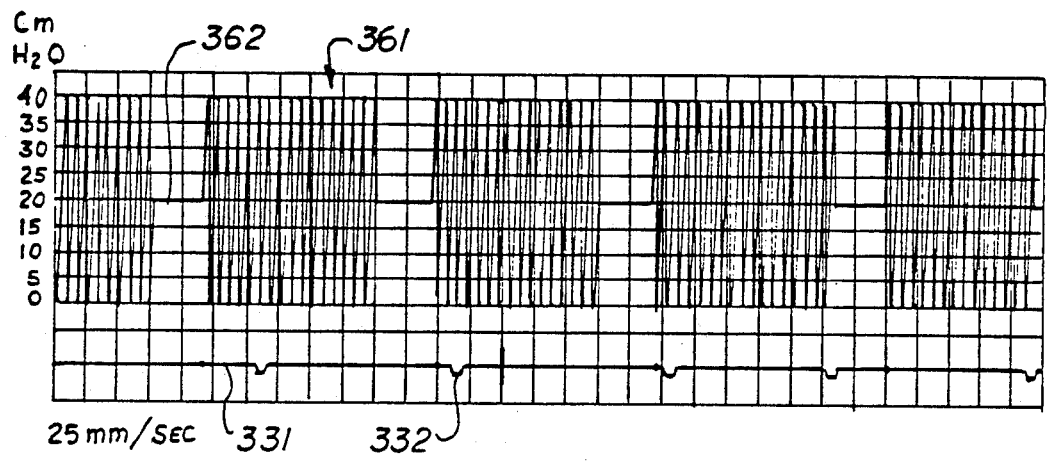
FIG. 8 shows an oscilloscope trace from a waveform analyzer connected to a ventilator of the present invention with the breathing circuit shown in FIG. 7 and utilizing a substantially constant mean pressure.
Figure 9:
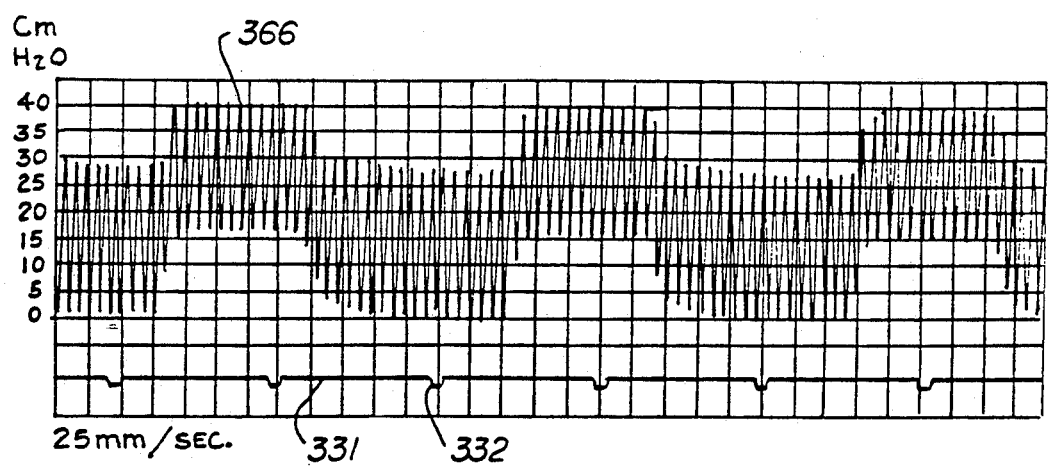
FIG. 9 shows an oscilloscope trace from a waveform analyzer connected to a ventilator using the breathing circuit shown in FIG. 7 with a sinusoidal mean pressure.

As the diaphragm 78 moves to the right as viewed in FIG. 7, a peak pressure rise of 40 centimeters of water is created as shown in FIG. 8. Upon opening of the outflow valve 351, the diaphragm 78 substantially instantaneously under the force of the counterspring, causes a sub-ambient pressure to be created to cause the pressure in the tubing 189 to drop down to 0 centimeters of water as shown in FIG. 8. Thus it can be seen that there is an instantaneous pressure rise and an instantaneous pressure drop from 40 centimeters of water to 0 centimeters of water in the breathing circuit at a predetermined frequency rate, as for example, 900 times a minute while holding a substantially constant mean pressure in the patient's airway above 0 as, for example, 20 centimeters of water as shown in FIG. 8. In this way, the functional residual capacity of the patient's lungs is increased mechanically with the addition of percussive ventilation supplied from the oscillator canister 41 to provide a dynamic functional residual capacity. From FIG. 8 it can be seen that oscillation is occurring from the mean pressure baseline 362 while maintaining the mean pressure in the lung. The lungs of the patient are, in effect, being percussed or shaken by the addition and subtraction of the small volumes of air produced by the oscillator resonator as, for example, 2 to 5 centimeters. In this way, it is possible to obtain a convectional flow of gas as well as diffusive flow of gases for ventilating the lungs of neonates with constant percussive oscillation while maintaining a variable CPAP. This is very desirable to minimize intracranial bleeding and also to inhibit barotrauma of the lungs of the neonatal patient. In FIG. 9, there is shown a neonatal waveform 366 in which a sinusoidal mean pressure is utilized.

From the foregoing, it can be seen that there has been provided a ventilator which is particularly adapted for cardiopulmonary intensive care and for weaning. It utilizes a closed circuit diaphragm oscillator which delivers and retrieves subtidal volumes through an independently selected baseline mean pressure. A high frequency positive/sub-ambient percussive waveform is transmitted symmetrically through a selected CPAP. With the use of breathing circuit options herein disclosed, the ventilator can be employed as a stand alone ventilator or as a slaving ventilator to impose a higher frequency oscillatory waveform upon a traditional convection ventilator to make possible universal cardiopulmonary management. Independent programming of time cycled ventilation is available. An independently selectable inspiratory ratio component or a constant inspiratory time with a selectable (variable) expiratory time can be provided. A rate selection withstanding calibration can be programmed from 1 to 55 breaths per minute. I/E ratios from 10:1 to 1:10 can be scheduled. The time cycled ventilator makes possible sinusoidal control over a selected baseline CPAP and/or traditional tidal volume delivery to enhance convection during continuous diffusive percussive oscillation and/or traditional time cycling of the ventilator. Neonatal, pediatric and adult programming utilizing different breathing circuits ca be scheduled.

What is claimed is:

1. In a ventilator adapted to be connected to a source of gas under pressure, a case, an inlet carried by the case and adapted to be connected to the source of gas, a pneumatic oscillator cartridge mounted in the case and having a body with an inlet and an outlet and a flow passage interconnecting the inlet and the outlet, diaphragm operated valve means mounted within the body and movable between open and closed positions for interrupting the flow of gas from the inlet to the outlet, a servo port in communication with the diaphragm operated valve means, means for supplying gas from the outlet to the servo port to operate the valve means, adjustable valve means for metering the flow of gas from the outlet to the servo port to provide cyclic operation of the oscillator cartridge, a patient adapter having an inlet, means supplying a continuous flow of gas to the inlet of the patient adapter, exhalation means connected to the inlet of the patient adapter for permitting gas to escape to ambient, pneumatic clutching means having an inlet and an outlet, means connecting the outlet of the oscillator cartridge to the inlet of the pneumatic clutching means, an oscillator canister having an inlet and an outlet, means coupling the outlet of the pneumatic clutching means to the inlet of the oscillator canister, means coupling the outlet of the oscillator canister to the inlet of the patient adapter, said oscillator canister having a shaft, a diaphragm mounted on the shaft and separating said canister into first and second chambers on opposite sides of the diaphragm with the first chamber being in communication with the inlet of the oscillator canister and the second chamber being in communication with the outlet of the oscillator canister, counterspring means mounted on said shaft, said oscillator canister serving to supply and withdraw small volumes of gas to and from the patient adapter, said small volumes of gas being superimposed upon the continuous flow of gas to the patient adapter whereby dynamic volumetric diffusive ventilation is supplied to the patient.

2. A ventilator as in claim 1 wherein the pneumatic clutching means causes said oscillator canister to operate at a constant stroke.

3. A ventilator as in claim 1 wherein said counterspring means comprises a counterspring mounted on the shaft on each side of the diaphragm.

4. A ventilator as in claim 1 wherein said diaphragm in the oscillation canister has an annular thin walled convolution therein with a thickness which is substantially less than the thickness of the remainder of the diaphragm.

5. A ventilator as in claim 1 wherein said exhalation means includes a body having an exhalation port, valve means mounted in said body movable between open and closed positions with respect to the exhalation port for controlling the flow of gas from the patient adapter through the exhalation port and spring means carried by the body for yieldably urging the valve member towards a closed position.

6. A ventilator as in claim 5 together with adjustable means carried by the body of the exhalation means for adjusting the force applied by the spring to the valve member to thereby provide a constant pressure against which the patient must breathe.

7. A ventilator as in claim 5 together with pneumatically operated means connected to the body for controlling the movement of the valve means.

8. A ventilator as in claim 7 wherein said pneumatic means for controlling the operation of the valve means includes a timing cartridge with a body with an inlet and an outlet and a flow passage interconnecting the inlet to the outlet, a valve member carried by the body of the timing cartridge and movable between open and closed positions with respect to the outlet, a servo port carried by the body of the timing circuit for supplying gas to the diaphragm and adjustable valve means for connecting the outlet of the timing cartridge to the servo port of the timing cartridge for controlling the operation of the timing cartridge.

9. A ventilator as in claim 5 together with means coupled to the inlet of the body of the exhalation means, and means for supplying gas to the inlet of the body so that the patient is forced to breathe against a constant positive airway pressure.

10. A ventilator as in claim 9 wherein said means for causing the patient to breathe against a constant positive airway pressure consists of a body having an inlet connected to the inlet of the case and having an outlet with a flow passage between the inlet and the outlet, adjustable diaphragm operated valve means for controlling the flow of gas from inlet to the outlet, a servo port carried by the body for supplying gas to the diaphragm operated means and means connecting the servo port of the body to the patient adapter whereby a constant positive airway pressure is provided to the patient.

11. A ventilator as in claim 1 together with overpressure governor means connected to the means for supplying gas continuously to the patient adapter and having a fail safe condition so that it will open to ambient in the event of an overpressure condition.

12. A ventilator as in claim 11 wherein said overpressure governor means includes exhalation valve means having a port open to ambient which in the event of interruption of flow of gas to the patient will permit the patient to obtain ambient air through said port open to ambient.

13. A ventilator as in claim 1 together with means for giving a visual indication of the metered flow of gas being supplied to the patient adapter.

14. A ventilator as in claim 1 together with pressure measuring means connected to the canister for monitoring selectively the peak-to-peak pressure generated in the canister.

15. A ventilator as in claim 14 wherein said means for monitoring the oscillator canister includes means for measuring the positive pressure rise and the sub-ambient pressure drop.

16. A ventilator as in claim 15 wherein the high frequency oscillation is maintained at a frequency of approximately 900 cycles per minute.

17. A ventilator as in claim 1 together with heated humidifier means for supplying humidified gases to the patient adapter.

18. A ventilator as in claim 1 wherein said oscillator canister supplies small volumes of gas at a frequency ranging from 300 to 1500 cycles per minute.

19. A ventilator as in claim 18 wherein said oscillator canister operates on a closed circuit of gas.

20. A ventilator as in claim 1 together with spoiler means coupled to the patient adapter for increasing the peak-to-peak pressure band width.

21. A ventilator as in claim 1 together with means for monitoring the pressures in the oscillator canister as well as peak positive and peak sub-ambient pressures.

22. A ventilator as in claim 1 wherein a timing cartridge is provided having a split timing circuit permitting independent synchronized uploading and downloading for establishing both negative and positive i/e and I/E ratios during cycling.

23. A ventilator as in claim 1 together with a pressurized governor connected to the patient adapter for supplying a continuous flow of gas to the patient adapter.

24. In a method for ventilating the airway of a patient from a source of gas under pressure comprising the steps of providing a canister having an inlet adapted to be coupled to the source of gas an outlet adapted to be coupled to the airway of the patient, providing a diaphragm in the canister having a central portion and a outer annular convoluted portion to provide a servoing chamber and a percussion chamber on opposite sides of the diaphragm, providing first and second countersprings respectively in the servoing chamber and percussion chamber on opposite sides of the central portion of the diaphragm, supplying gas from the source of gas under pressure to the servoing chamber to provide a pneumatic force to cause movement of the convoluted portion of the diaphragm in a first direction followed by the central portion of the diaphragm against the force of the second counterspring until a centered position is achieved, depressurizing the servoing chamber to cause motion of the convoluted portion of the diaphragm in a second direction followed by the central portion of the diaphragm against the force of the first counterspring until a centered position is achieved and thereby supplying a plurality of small volumes of gas with rapid changes in pressure to the airway of the patient during each inspiratory phase, and withdrawing a plurality of small volumes of gas with rapid changes in pressure from the airway of the patient during each expiratory phase whereby dynamic diffusive ventilation is supplied to the airway of the patient.

25. A method as in claim 24 wherein the small volumes of gas are constant volumes.

26. A method as in claim 24 wherein the gases are supplied to and withdrawn from the airway of the patient at a frequency ranging from 200 to 1500 cycles per minute.

27. A method as in claim 24 together with the step of causing the patient to exhale in the expiratory phase against a positive pressure.

28. A method as in claim 24 together with the step of timing when the exhalation phase can commence.

29. A method as in claim 27 together with a step of providing a constant positive pressure.

30. A method as in claim 24 together with the step of measuring peak-to-peak pressures in the airway of the patient.

31. A ventilator adapted to be connected to a source of gas under pressure and to a patient airway; means adapted to be coupled to the patient airway for supplying gas under pressure to provide a flow of gas to the patient airway during the inspiratory phase, means adapted to be coupled to the patient airway permitting gases from the airway of the patient to be discharged to ambient; and means for supplying small volumes of gas with rapid changes in pressure to the patient's airway and for withdrawing small volume's of gas with rapid changes in pressure from the patient's airway, said means for supplying and withdrawing comprising an oscillator having a housing which defines a space with an inlet and an outlet in communication with the space, the outlet being adapted to be coupled to the patient airway, a diaphragm having first and second sides mounted within the housing serving to divide the space in the housing into a first servoing chamber and second percussion chamber with the first servoing chamber being in communication with the inlet and with the second percussion chamber being in communication with the outlet said diaphragm having a central portion and an annular convoluted portion disposed outwardly from the central portion, first and second yieldable spring means disposed respectively on the first and second sides of the diaphragm and servoing to yieldably retain the diaphragm in a centered position, pneumatic means for supplying pulses of gas to the first servoing chamber to cause repeated movement of the convoluted portion of the diaphragm in one direction followed by the central portion against the force of the yieldable means in accordance with the pulses of gas the movement of said diaphragm with respect to said second percussion chamber causing the supplying of a plurality of small volumes of gas with rapid changes in pressure to the patient airway superimposed upon the flow of gas to the airway of the patient during each inspiratory phase and causing the withdrawing of small volumes of gas with rapid changes in pressure from the airway of the patient by permitting repeated movement of the convoluted portion of the diaphragm followed by the central portion in an opposite direction against the force of the yieldable means during the times when pulses of gas are not being supplied to the servoing chamber during each expiratory phase whereby diffusive ventilation is provided for the patient.

32. A ventilator as in claim 31 together with a shaft secured to said central portion of the diaphragm, guide means carried by the housing for guiding the movement of the shaft as the diaphragm is moved and wherein said springs are disposed on said shaft.

33. A ventilator as in claim 32 wherein said diaphragm, said shaft and said springs have a low inertia with respect to reciprocatorial movement of the diaphragm to permit a rapid changeover in the movement of the diaphragm in opposite directions whereby rapid pressure changes are created in a transition from supplying a small volume of gas to withdrawing a small volume of gas.

34. A ventilator as in claim 31 wherein said convoluted portion of the diaphragm is provided with an annular thin-walled convolution having a wall thickness which is substantially less than the thickness of the central portion of the diaphragm.

35. A ventilator as in claim 31 wherein said pneumatic means includes a venturi-like passage for increasing the flow of gas into the first chamber when gas is supplied to the pneumatic means.

36. A ventilator as in claim 31 wherein said pneumatic means includes a cylindrical hollow body having a cylindrical passage extending therethrough, said body having an exhalation port in communication with the cylindrical passage, a venturi body slidably mounted with the body and spring means for yieldably urging said venturi body into sealing engagement with the body to close off said exhalation port, said venturi body having a venturi-like passage therein and an inlet in communication with the venturi-like passage, and means carried by the body for supplying gas from the source of gas to the inlet in communication with the venturi-like passageway.

* * * * *